United States Patent
Fujisawa

(10) Patent No.: US 7,166,272 B2
(45) Date of Patent: Jan. 23, 2007

(54) ORAL PREPARATION

(75) Inventor: Koichi Fujisawa, Osaka (JP)

(73) Assignee: Sunstar Inc., Osaka (JP)

( * ) Notice: Subject to any disclaimer, the term of this patent is extended or adjusted under 35 U.S.C. 154(b) by 381 days.

(21) Appl. No.: 10/481,853

(22) PCT Filed: Jul. 5, 2002

(86) PCT No.: PCT/JP02/06869

§ 371 (c)(1),
(2), (4) Date: Dec. 22, 2003

(87) PCT Pub. No.: WO03/003994

PCT Pub. Date: Jan. 16, 2003

(65) Prior Publication Data

US 2004/0146465 A1  Jul. 29, 2004

(30) Foreign Application Priority Data

Jul. 5, 2001 (JP) .............................. 2001-204791
Jul. 5, 2001 (JP) .............................. 2001-204792

(51) Int. Cl.
*A61K 8/46* (2006.01)
*A61Q 11/00* (2006.01)

(52) U.S. Cl. .............................. 424/56; 424/52; 424/54

(58) Field of Classification Search ..................... None
See application file for complete search history.

(56) References Cited

U.S. PATENT DOCUMENTS

| | | |
|---|---|---|
| 4,978,684 A | 12/1990 | Cerami et al. |
| 5,078,988 A | 1/1992 | Lin et al. |
| 5,096,703 A | 3/1992 | Cerami et al. |
| 5,128,122 A | 7/1992 | Cerami et al. |
| 5,154,915 A | 10/1992 | Weber et al. |
| 5,427,770 A | 6/1995 | Viccaro et al. |
| 5,589,160 A * | 12/1996 | Rice ..................... 424/49 |
| 5,908,612 A | 6/1999 | Dailey et al. |
| 5,932,191 A | 8/1999 | Chevallier et al. |
| 6,521,214 B1 | 2/2003 | Amiche et al. |

FOREIGN PATENT DOCUMENTS

| | | |
|---|---|---|
| EP | 0 327 919 | 8/1989 |
| EP | 0 371 551 | 6/1990 |
| EP | 0 373 688 | 6/1990 |
| EP | 0 376 363 | 7/1990 |
| EP | 0 518 608 A1 | 12/1992 |
| JP | 01-125315 | 5/1989 |
| JP | 02-056413 | 2/1990 |
| JP | 02-200618 | 8/1990 |
| JP | 02-209805 | 8/1990 |
| JP | 02-223512 | 9/1990 |
| JP | 03-038517 | 2/1991 |
| JP | 05-163126 | 6/1993 |
| JP | 10-017443 | 1/1998 |
| JP | 2000-053547 | 2/2000 |
| JP | 2000-505416 | 5/2000 |
| JP | 2000-319148 | 11/2000 |
| WO | WO 99/63961 | 12/1999 |

OTHER PUBLICATIONS

Machine translation of JP-2000-053547 (Feb. 22, 2000).*
Supplementary European Search Report issued on the corresponding European Patent Application No. 02 74 1422, dated Apr. 6, 2006.

* cited by examiner

*Primary Examiner*—Frederick Krass
(74) *Attorney, Agent, or Firm*—Knobbe, Martens Olson & Bear LLP

(57) ABSTRACT

An oral composition comprising 0.5 to 10% by weight of an abrasive precipitated silica having a 50 percentile (d50) of particle diameter being 5 μm or less, a 90 percentile (d90) of particle diameter being 15 μm or less and an RDA value of 120 or more, and 0.01 to 5% by weight of at least one of sulfosuccinate surfactants represented by general formula (1):

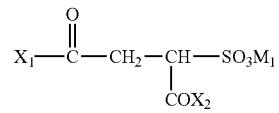

[wherein either $X_1$ or $X_2$ is $R_1O$—$(AO)_n$— or the like and the other is $M_2O$—; $M_1$ and $M_2$ are the same or different and each represent hydrogen, alkali metal, etc.; $R_1$ is $C_{8-22}$ alkyl, etc.; AO is $C_{2-3}$ oxyalkylene and the average number of moles of AO addition polymerization, "n", is 0 to 20; and B is —NH— etc.]

17 Claims, No Drawings

ORAL PREPARATION

This application is a 371 of PCT/JP02/06869, filed Jul. 5, 2002.

TECHNICAL FIELD

The present invention relates to an oral composition containing a sulfosuccinate surfactant.

BACKGROUND OF THE INVENTION

Tooth discoloration results from formation of chromogenic substances, and their deposition on the surface of teeth, called "stain", and causes a serious problem of aesthetic appreciation. Staining may be attributable to the contact of teeth with bactericides, such as chlorhexidine; tannin and analogous substances contained in tea, etc; and metals such as an iron. Methods of inhibiting stain formation and suppressing stain deposition to teeth have been suggested for efficiently preventing tooth discoloration.

As a method of inhibiting stain formation, Japanese Unexamined Patent Publication No. 1989-125315 discloses inhibiting stain occurrence due to tannin-based substances by polystyrene sulfonate; Japanese Unexamined Patent Publication No. 1990-56413 discloses inhibiting stain formation by blocking nonenzymatic browning reactions. However, these methods target solely a specific stain and thus are not effective against all stain types. Japanese Unexamined Patent Publication No. 1998-17443 discloses employing a sulfosuccinate surfactant for oral compositions as a stain-formation-inhibitor. For methods of suppressing stain deposition, Japanese Unexamined Patent Publication Nos. 1990-200618, 1990-209805 and 1990-223512 disclose suppressing stain deposition by coating a tooth surface with aminoalkyl silicone and Japanese Unexamined Patent Publication Nos. 1991-38517 and 1993-163126 disclose employing fluoroalkyl phosphoric acid esters to attain the same effect. However, these references disclose methods of either inhibiting stain formation or suppressing stain deposition. There have been no findings about oral compositions which can both inhibit stain formation and suppress stain deposition.

An object of the present invention is to provide an oral composition which is endowed with effects of inhibiting stain formation and suppressing stain deposition, and thereby effectively prevents tooth discoloration.

DISCLOSURE OF THE INVENTION

In view of the above-described present circumstances, the inventors carried out intensive research and found a specific oral composition which is endowed with stain formation inhibitory and stain deposition suppressive effects. More specifically, the oral composition comprises 0.5 to 10% by weight of an abrasive precipitated silica having a 50 percentile ($d_{50}$) particle diameter being 5 μm or less, a 90 percentile ($d_{90}$) of particle diameter being 15 μm or less and an RDA value of 120 or more and 0.01 to 5% by weight of a sulfosuccinate surfactant. The inventors have accordingly completed the present invention.

More specifically, the present invention provides an oral composition relating to the following items.

1. An oral composition comprising 0.5 to 10% by weight of an abrasive precipitated silica having a 50 percentile ($d_{50}$) of particle diameter being 5 μm or less, a 90 percentile ($d_{90}$) of particle diameter being 15 μm or less and an RDA value of 120 or more, and 0.01 to 5% by weight of at least one sulfosuccinate surfactant represented by general formula (1):

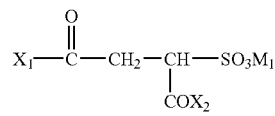

wherein either $X_1$ or $X_2$ is $R_1O—(AO)_n—$ or $R_1CO—B—(AO)_n—$ and the other is $M_2O—$; $M_1$ and $M_2$ are the same or different and each represent hydrogen, alkali metal, alkaline earth metal, ammonium, or alkanolamine; $R_1$ is alkyl or alkenyl with 8 to 22 carbons; AO is oxyalkylene with 2 or 3 carbons and the average number of moles of AO addition polymerization, "n", is 0 to 20; and B is —NH— or a monoalkanolamine residue with 2 or 3 carbons.

2. An oral composition according to claim 1, wherein the average number of moles of AO addition polymerization, "n", of sulfosuccinate surfactant represented by general formula (1) is 0 to 7.
3. An oral composition according to claim 1 wherein a carbon number of an alkyl group or an alkenyl group of sulfosuccinate surfactant represented by general formula (1) is 10 to 14.
4. An oral composition according to claim 1 wherein $M_1$ and $M_2$ of sulfosuccinate surfactant represented by general formula (1) are sodium.
5. An oral composition according to claim 1 wherein an RDA value of the abrasive precipitated silica is 130 to 200.
6. An oral composition according to claim 1 wherein the amount of the abrasive precipitated silica is 1 to 5% by weight.
7. An oral composition according to claim 1 further comprising an abrasive precipitated silica having an RDA value of 40 to 110.
8. An oral composition according to claim 7 wherein the amount of the abrasive precipitated silica having an RDA value of 40 to 110 is 3 to 25% by weight.
9. An oral composition according to claim 1 wherein saccharin sodium and stevioside are further contained in the weight ratio of saccharin sodium to stevioside of 1:1 to 8:1 and their total amount is 0.01 to 1% by weight.
10. An oral composition according to claim 1 further comprising at least one member selected from the group consisting of vanillin, anethole, and benzylsuccinate.
11. An oral composition according to claim 9 further comprising at least one member selected from the group consisting of vanillin, anethole, and benzylsuccinate.

Hereinafter, the present invention will be described in more detail.

The sulfosuccinate surfactant used in the present invention is not limited insofar as it is a sulfosuccinate monoester represented by the following general formula (1).

General Formula (1):

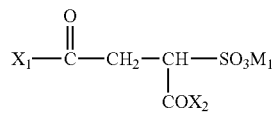

[wherein either $X_1$ or $X_2$ is $R_1O—(AO)_n—$ or $R_1CO—B—(AO)_n—$ and the other is $M_2O—$; $M_1$ and $M_2$ are the same or different and each represent hydrogen, alkali metal, alkaline earth metal, ammonium, or alkanolamine; $R_1$ is alkyl or alkenyl with 8 to 22 carbons; AO is oxyalkylene with 2 or 3 carbons, the average number of moles of AO addition polymerization, "n", is 0 to 20; and B is —NH— or a monoalkanolamine residue with 2 or 3 carbons.]

In the sulfosuccinate monoester represented by general formula (1), $R_1$ is a naturally derived or synthetic linear or branched alkyl or alkenyl group with 8 to 22 carbons. For example, lauryl, cocoyl, myristyl, stearyl, synthetic $C_{12}$–$C_{14}$ alkyl, isononyl, isododecyl, octenyl, dodecenyl, etc., can be mentioned. The longer the carbon chain of $R_1$, the more reduced is the bitterness and stimulus, while the shorter the carbon chain of $R_1$, the higher the stain formation inhibitory effect. Thus, the carbon number of $R_1$ is preferably 10 to 16, and more preferably 12 to 14. Synthetic $C_{12}$–$C_{14}$ alkyl or a combination of lauryl and myristyl is most preferred.

$M_1$ and $M_2$ may be the same or different, and examples thereof include hydrogen, alkali metals, alkaline earth metals, ammonium or alkanolamines. Examples of alkali metals include sodium, potassium, etc. Examples of alkali earth metals include magnesium, etc. Examples of alkanolamines include monoethanolamine, diethanolamine, triethanolamine, etc. Among these, sodium and magnesium are preferred as $M_1$ and $M_2$, and sodium is most preferred.

The AO group is an oxyalkylene group with 2 or 3 carbons, and is preferably oxyethylene group. The average number of moles of AO addition polymerization, "n", is preferably about 0 to about 20. The stain formation inhibitory effect is increased and bitterness is also reduced as the average number of moles of AO addition polymerization, "n", becomes smaller, and thus "n" is preferably about 0 to about 7, and most preferably about 0 to about 2. When the average number of moles of AO addition polymerization is 0, the sulfosuccinate monoester does not contain any oxyalkylene groups.

Examples of sulfosuccinate monoesters represented by general formula (1) are disodium polyoxyethylene (7 mols) lauryl sulfosuccinate, disodium polyoxyethylene (2 mols) laurylsulfosuccinate, disodiumpolyoxyethylene (1 mol) lauryl sulfosuccinate, disodium lauryl sulfosuccinate, disodium polyoxyethylene (7 mols) myristyl sulfosuccinate, disodium polyoxyethylene (2 mols) alkyl ($C_{12-14}$) sulfosuccinate, disodium polyoxyethylene (1 mol) alkyl ($C_{12-14}$) sulfosuccinate, disodium alkyl ($C_{12-14}$) sulfosuccinate, magnesium polyoxyethylene (2 mols) lauryl sulfosuccinate, magnesium polyoxyethylene (2 mols) alkyl ($C_{12-14}$) sulfosuccinate, ditriethanolamine polyoxyethylene (7 mol) myristyl sulfosuccinate, etc. Examples of sulfosuccinate monoesters represented by general formula (2) are disodium oleamid sulfosuccinate, disodium lauramid polyoxyethylene (5 mols) sulfosuccinate, disodium polyoxyethylene (2 mols) cocoyl isopropanol amide sulfosuccinate, etc.

The most suitable sulfosuccinate monoester is a sodium salt of general formula (1) in which $R_1$ is an alkyl group with 12 to 14 carbons, the AO group is the oxyethylene group, and the average number of moles of AO addition polymerization, "n", is about 0 to about 2. Examples thereof are disodium polyoxyethylene (2 mols) alkyl ($C_{12-14}$) sulfosuccinate, disodium polyoxyethylene (1 mol) alkyl ($C_{12-14}$) sulfosuccinate, and disodium alkyl ($C_{12-14}$) sulfosuccinate.

The sulfosuccinates represented by general formula (1) may be used alone or in combination of two or more.

In general, the amount of sulfosuccinate monoester represented by general formula (1) is preferably about 0.01 to about 5% based on the total weight of the composition, and more preferably about 0.1 to about 2% by weight. The stain formation inhibitory effect cannot be sufficiently obtained when the amount is below 0.01% by weight, while palatability is impaired if it exceeds about 5% by weight.

The present invention requires employing about 0.5 to about 10%, based on the total weight of the composition, of an abrasive precipitated silica in which $d_{50}$ is about 5 μm or below, $d_{90}$ is about 15 μm or below and has an RDA value of 120 or more (the precipitated silica is hereinafter sometimes referred to as "first silica").

Generally, precipitated silica is produced as follows. A dilute alkali metal silicate (for example, sodium silicate) is reacted with strong acid (for example, sulfuric acid) under conditions which preclude aggregation to form sol and gel, usually under acidic conditions. The reactant is then subjected to filtering, washing, and drying, and thereafter, is milled to obtain a powdery product with desired diameter. The present invention can employ a precipitated silica prepared according to a known procedure. The precipitated silica is used as an abrasive agent in the present invention since it is more favorable than silica gel in terms of low hygroscopicity, ease of handling and low cost.

An abrasive precipitated silica prepared according to a known procedures can be used as the first silica of the present invention.

The amount of first silica is 0.5 to 10% by weight in the composition, preferably about 0.5 to about 6% by weight, more preferably about 1 to about 5% by weight, and still more preferably about 2 to about 4% by weight. When the amount is less than 0.5% by weight, stain deposition may not be sufficiently suppressed; when the amount is more than 10% by weight, teeth may be damaged.

The values of $d_{50}$ and $d_{90}$ were measured with a Malvern Mastersizer equipped with a low output He/Ne laser and based on the Fraunhofer diffraction principle. The value of $d_{50}$ is preferably about 4.5 μm or less, and more preferably about 4 μm or less. The lower limit of $d_{50}$ is not limited insofar as the desired effects of the present invention are not adversely affected, but is usually about 3 μm or less, and preferably about 1 μm. The value of $d_{90}$ is preferably about 13 μm or less, and more preferably about 10 μm or less. The lower limit of $d_{90}$ is not limited insofar as the desired effects of the present invention are not reduced, but is usually about 8 μm or less, and preferably about 5 μm.

The RDA value is an abbreviation of Radioactive Dentin Abrasion value and can be determined, for example, by the procedure of hefferen et al. (J. Dent. Res., Vol. 55, No. 4, 563–573, 1976). The RDA value is preferably about 130 or more, and more preferably about 150 or more. The upper limit of the RDA value is not especially limited, but usually is about 250, and preferably about 200. Therefore, the preferable range of the RDA values is about 120 to about 250, more preferably about 130 to about 200, and still more preferably about 150 to about 200.

The oral composition of the present invention can contain, in addition to the first silica, an abrasive precipitated silica having an RDA value of about 40 to about 110 (hereinafter sometimes referred to as "second silica").

Use of the second silica in combination with the first silica further improves stain formation inhibitory effects of the composition, and is thus advantageous.

The RDA value of the second silica is usually about 40 to about 110, preferably about 60 to about 110, more preferably about 80 to about 110, and still more preferably about 85 to about 110.

The second silica is not limited insofar as the RDA value is within the above-described ranges. It is preferable that $d_{50}$ of particle diameter of the second silica is about 20 μm or less, and more preferably about 15 μm or less. The lower limit of $d_{50}$ is not limited, and is usually about 10 μm or less, and preferably about 8 μm or less.

The amount of the second silica is preferably about 3 to about 25% based on the total weight of the composition, more preferably about 8 to about 20% by weight, still more preferably about 10 to about 20% by weight, and most preferably about 15 to about 20% by weight.

The total amount of the first silica and the second silica in the oral composition of the invention is preferably about 5 to about 30% by weight, more preferably about 10 to about 25% by weight, still more preferably about 12 to about 23% by weight, and most preferably about 17 to about 23% by weight. The weight ratio of the first silica to the second silica is preferably about 1:20 to 1:1, more preferably about 1:10 to 1:2, and still more preferably about 1:10 to 1:3.

Examples of silica contents in the composition of the invention are as follows:

About 1 to about 5% based on the total weight of the composition of the first silica having an RDA value of about 150 to about 200 and about 10 to about 20% based on the total weight of the composition of the second silica having an RDA value of about 85 to about 110 are mixed so that the total amount of the first silica and the second silica is 12 to 23% based on the total weight of the composition and the weight ratio of the first silica to the second silica is 1:10 to 1:2.

About 2 to about 4% based on the total weight of the composition of the first silica having an RDA value of about 150 to about 200, $d_{50}$ of about 3 to about 4 μm and $d_{90}$ of about 8 to about 10 μm, and about 15 to about 20% based on the total weight of the composition of the second silica having an RDA value of about 85 to about 110 and $d_{50}$ of about 10 to about 15 μm are mixed so that the total weight of the first silica and the second silica is 17 to 23% based on the total weight of the composition and the weight ratio of the first silica to the second silica is 1:8 to 1:3.

The oral composition of the present invention may be formulated into forms such as a tooth powder, toothpaste, gel, prophylaxis paste, pasta, chewing gum, tablet, etc., according to the known procedures. A dentifrice is particularly preferable from a practical viewpoint.

In addition to the above-described sulfosuccinate surfactant and abrasive precipitated silica, the composition according to the invention can contain, depending on its form, water, lower alcohols, higher alcohols, and other additives commonly employed in the art. Such additives include abrasives other than the abrasive precipitated first silica and second silica, vehicles, foaming agents, binders, pH adjusting agents, surfactants other than the sulfosuccinate surfactants represented by general formulae (1) and (2), humectants, sweeteners, flavors, antiseptics, colorants, and various active ingredients. The amount of the additives can be appropriately determined insofar as they do not deteriorate the effects of the present invention.

The amount of water can be appropriately determined by depending on the form of the agent, etc., and is usually about 0 to about 70%, and preferably about 10 to about 50%, based on the total weight of the composition. The amount of lower alcohol is usually about 0 to about 10%, and preferably about 0 to about 5% based on the total weight of the composition. The amount of higher alcohol is usually about 0 to about 70% by weight, and preferably about 10 to about 50% by weight.

The abrasives other than the above-described abrasive precipitated first and second silicas include dicalcium phosphate dihydrate, dicalcium phophate anhydrous, calcium phosphate, tricalcium phosphate, calcium carbonate, calcium pyrophosphate, aluminium hydroxide, alumina, silica gel, aluminium silicate, abrasive precipitated silica other than the above-mentioned abrasive precipitated first and second silicas, insoluble sodium metaphosphate, trimagnesium phosphate, magnesium carbonate, calcium sulfate, polymethylmethacrylate, bentonite, zirconium silicate, hydroxyapatite, synthetic resins, etc. These abrasives may be used alone or in combination of two or more. The amount of abrasive other than the above-mentioned abrasive precipitated first and second silicas is usually about 5 to about 90% based on the total weight of the composition and about 5 to about 50% by weight in the case of a toothpaste.

Examples of vehicles include fumed silica, thickening silica (generally with an RDA value of about 30 or less) and cellulose powder, such as crystalline cellulose, etc. Among these fumed silica and thickening silica are preferred. The amount of vehicle is usually about 0.1 to about 30%, and preferably about 0.5 to about 10%, based on the total weight of the composition.

Examples of foaming agents include anionic surfactants other than the sulfosuccinate surfactants represented by general formula (1). For example, the following can be mentioned: higher alkyl sulfate salts having alkyl groups including 8 to 18 carbons, such as sodium lauryl sulfate, sodium myristyl sulfate, etc.; long-chain N-acylamino acid salts, α-olefin sulfonate salts, sodium higher fatty acid monoglyceride monosulfate, N-methyl-N-palmitoyl taurinates, sodium N-acylsarcosinates, N-acylglutamates, sodium N-methyl-N-acyl taurinates, sodium N-methyl-N-acylalanates, sodium α-olefin sulfonates, etc. Many of these anionic surfactants can remove stains to a high degree through chemical dissolution. In particular, sodium lauryl sulfate synergetically enhances the effect of suppressing stain formation when mixed, and is thus preferable. Such anionic surfactants may be used alone or in combination of two or more. The amount of the anionic surfactants other than the sulfosuccinate surfactants represented by general formula (1) is usually about 0.001 to about 5%, and preferably about 0.01 to about 2%, based on the total weight of the composition.

In addition to anionic surfactants, the composition of the present invention can further contain nonionic surfactants, amphoteric surfactants, and cationic surfactants as usually used for oral compositions. Examples of such surfactants include nonionic surfactants such as polyoxyethylene fatty acid esters (for example, polyoxyethylene sorbitan fatty acid ester such as polyoxyethylene sorbitan monolaurate, etc.), polyoxyethylene hydrogenated castor oil, lauric acid monoethanolamide, myristic acid monoethanolamide, polyoxyethylene higher alcohol ethers, polyoxyethylene polyoxypropylene copolymers, polyoxyethylene polyoxypropylene fatty acid ester alkyl glycosides (for example, alkyl chain: about $C_8$ to about $C_{16}$), polyglyceryl fatty acid esters (for example, alkyl chain of the fatty acid moiety: about $C_8$ to about $C_{16}$), sucrose fatty acid esters (for example, alkyl chain of the fatty acid moiety: about $C_8$ to about $C_{16}$), etc; amphoteric surfactants, such as N-alkyl diaminoethylglycines, alkyl betaines, fatty acid amidopropyl betaines (for example, alkyl chain of the fatty acid moiety: about $C_8$ to about $C_{16}$), alkyl sulfo betaines, alkyl betaine imidazonium betaines, etc.; cationic surfactants such as alkyltrimethylammonium chlorides, alkyltrimethylammonium bromides, alkyldimethylammonium chlorides, etc. Among these, polyoxyethylene hydrogenated castor oil and alkyl glycoside are preferred.

The amount of the surfactant other than anionic surfactants and sulfosuccinate surfactants represented by general formula (1) is usually about 0.001 to about 5%, and preferably about 0.01 to about 2%, based on the total weight of the composition.

Examples of binders include cellulose derivatives such as carboxymethylcellulose sodium, etc.; alkali metal alginates such as sodium alginate, etc.; gums such as propylene glycol alginate, xanthane gum, tragacanth gum, karaya gum, arabic gum, carrageenan, etc.; synthetic binders such as polyvinyl alcohol, sodium polyacrylate, carboxy vinyl polymers, polyvinyl pyrrolidone, etc. Such binders may be used alone or in combination of two or more. The amount of binder is usually about 0.3 to about 5% based on the total weight of the composition.

Examples of flavors include menthol, carvone, anethole, vanillin, benzylsuccinate, eugenol, methyl salicylate, limonene, ocimene, n-decyl alcohol, citronellol, α-terpineol, methyl acetate, citronellyl acetate, methyl eugenol, cineol, linalool, ethyl linalool, vanillin, thymol, etc. These may be used alone, and may be used as vegetable extracts, such as essential oils containing the above-mentioned flavor (for example, vegetable extracts as shown below) Examples of flavors include vegetable extracts such as thyme oil, nutmeg oil, spearmint oil, peppermint oil, anise oil, star anise oil, fennel oil, lemon oil, orange oil, sage oil, rosemary oil, cinnamon oil, pimento oil, diatom oil, perilla oil, wintergreen oil, clove oil, eucalyptus oil, basil oil, tea tree oil, davana oil, vanilla oil, cranberry oil, etc. Flavors may be used alone or in combination of two or more. The amount of flavor can be suitably determined according to the kind of the flavor used, etc., and is usually about 0.05 to about 10%, and preferably about 0.1 to about 5% based on the total weight of the composition.

The composition of the present invention preferably contains at least one of vanillin, anethole and benzylsuccinate among these flavors. The odor peculiar to sulfosuccinate surfactants is masked by mixing the above-described flavors into the composition of the present invention and is thus preferable. The amount of at least one of vanillin, anethole, and benzylsuccinate is usually about 0.0001 to about 1%, preferably about 0.001 to about 0.5%, more preferably about 0.001 to about 0.2% based on the total weight of the composition.

Examples of sweeteners include saccharin, saccharin sodium, stevioside, acesulfame K, glycyrrhizin, perillartine, thaumatin, aspartylphenylalanine methyl ester, xylitol, paratinose, palatinit, erythritol, maltitol, etc. The sweeteners may be used alone or in combination of two or more. The amount of sweetener may be suitably determined according to desired sweetness, and is usually 0.01 to 5% based on the total weight of the composition.

The composition of the present invention preferably contains saccharin sodium and stevioside among the above-described sweeteners. In particular, the weight ratio of saccharin sodium to stevioside is in the range of about 1:1 to 8:1 (preferably in the range of about 1:1 to 4:1), and the total of saccharin sodium and stevioside is about 0.01 to about 1% (preferably about 0.02 to about 0.5%) based on the total weight of the composition. Stevioside may be used alone or may be used as vegetable extracts containing stevioside (for example, stevia extract).

The combination of saccharin sodium and stevioside is excellent in suppressing the bitterness peculiar to sulfosuccinate surfactants, and is thus preferable. Bitterness peculiar to sulfosuccinate surfactants can be sufficiently reduced when the weight ratio of saccharin sodium and stevioside is within the above-mentioned range, and is thus preferable. Bitterness is sufficiently suppressed when the total amount of saccharin sodium and stevioside is 0.01% by weight or more, while sweetness is not too strong and palatability is excellent when the total amount thereof is 1% or less by weight, and thus the total amount is preferable.

Examples of humectants include sorbitol solution, glycerin, ethylene glycol, propylene glycol, 1,3-butylene glycol, polyethylene glycol, polypropylene glycol, lactitol, etc. Humectants may be used alone or in combination of two or more. The amount of humectant is usually about 5 to about 70% based on the total weight of the composition.

Examples of pH adjusting agents include phosphoric acids and salts thereof (sodium phosphates, sodium hydrogenphosphates, etc.), citric acid and salts thereof (sodium, etc.), phosphoric acid and salts thereof, malic acid and salts thereof, gluconic acid and salts thereof, maleic acid and salts thereof, aspartic acid and salts thereof, gluconic acid and salts thereof, succinic acid and salts thereof, glucuronic acid and salts thereof, fumaric acid and salts thereof, glutamic acid and salts thereof, adipic acid and salts thereof, hydrochloric acid, sodium hydroxide, potassium hydroxide, sodium silicate, etc. pH adjusting agents may be used alone or in combination of two or more. The amount of pH adjusting agent is not limited insofar as the desired pH is attained, but is usually about 0.01 to about 5%, and preferably about 0.1 to about 3% based on the total weight of the composition. The pH of the composition of the present invention is not limited insofar as effects of the present invention can be attained, but is usually about 4 to about 10, and preferably about 5.5 to about 9.

Examples of antiseptics include benzoic acid salts, such as sodium benzoate; parabens, such as methylparaben, butylparaben, etc. Antiseptics may be used alone or in combination of two or more. The amount of antiseptic is usually about 0.01 to about 3% based on the total weight of the composition.

Examples of colorants include authorized dyes, such as blue No. 1, yellow No. 4, red No. 202, green No. 3, etc.; mineral-based coloring agents, such as ultramarine blue, strengthening ultramarine blue, Prussian blue, etc.; titanium oxide, etc. Colorants may be used alone or in combination of two or more. The amount of colorant is usually about 0.0001 to about 1% based on the total weight of the composition.

Examples of active ingredients include cationic bactericides such as quaternary ammonium salts (for example, cetylpyridinium chloride, benzethonium chloride, distearyldimethylammonium chloride, stearyldimethylbenzylammonium chloride, stearyltrimethylammonium chloride, lauryltrimethylammonium chloride, laurylpyridinium chloride, etc.), biguanide based bactericides (for example, chlorhexidine hydrochloride, chlorhexidine acetate, chlorhexidine gluconate, alexidine hydrochloride, alexidine acetate, alexidine gluconate, etc.), etc.; anionic bactericides, such as sodium N-lauroyl salcosinate, etc.; non-ionic bactericides such as triclosan, isopropylmethylphenol, etc.; enzymes such as dextranase, amylase, papain, protease, mutanase, lysozymes, lytic enzymes, etc.; zinc compounds such as zinc oxide, zinc chloride, etc.; fluorides such as alkali metal monofluorophosphates (for example, sodium monofluorophosphate, potassium monofluorophosphate, etc.), sodium fluoride, stannous fluoride, etc.; tranexamic acid, ε-aminocaproic acid, aluminium chlorohydroxyl allantoin, dihydrocholesterol, vitamin-E derivatives such as tocopherol acetate, etc., glycyrrhizin salts, glycyrrhetic acid, glycerophosphate, chlorophyll, potassium nitrate, sodium chloride, callopeptide, soluble inorganic phosphoric acid compounds, etc. Examples of soluble inorganic phosphoric acid compounds include compounds represented by the following general formulae (2) and (3):

$$M_{m+2}P_mO_{3m+1} \quad \text{General formula (2):}$$

[wherein M represents Na or K, and m is an integer of 2 or more.]

$$(MPO_3)_l \quad \text{General formula (3)}$$

[wherein M represents Na or K, and l is an integer of 3 or more.]

In the above general formulae, m is usually an integer of 2 or more, and preferably an integer of 2 to 6, and l is usually an integer of 3 or more, and preferably an integer of 3 to 6.

Examples of compounds represented by general formula (2) include sodium pyrophosphate, potassium pyrophosphate, sodium tripolyphosphate, etc.

Examples of compounds represented by general formula (3) include sodium tetrametaphosphate, sodium hexametaphosphate, etc.

Active ingredients may be used alone or in combination of two or more. The amount of active ingredients is not limited insofar as the desired effect can be attained, and the amount can be suitably determined according to the kind of the active ingredient used, etc. The amount of active ingredients is usually about 0.001 to about 30% based on the total weight of the composition, and preferably about 0.01 to about 20% by weight.

BEST EMBODIMENT FOR CARRYING OUT THE INVENTION

The present invention is explained in further detail with reference to Examples and Comparative Examples. The scope of the invention is not limited by these Examples, however. In the following Examples and Comparative Examples, percentages are all by weight unless otherwise specified.

The following Examples and Comparative Examples employ abrasive precipitated silica as shown below:

Abrasive precipitated silica A; $d_{50}=3.5$ μl, $d_{90}=9.5$ μm, RDA value=180;

Abrasive precipitated silica B; $d_{50}=10$ μm, $d_{90}=30$ μm, RDA value=90; and Abrasive precipitated silica C; $d_{50}=4.0$ μm, $d_{90}=10$ μm, RDA value=130.

The abrasive precipitated silicas A and C belong in the "the first silica", while the abrasive precipitated silica B belongs in the "the second silica".

EXAMPLES I-1 TO I-4 AND COMPARATIVE EXAMPLES I-1 TO I-4

Toothpastes were prepared by mixing the components shown below according to a known procedure, and was used for evaluating effects of inhibiting stain formation and of suppressing stain deposition.

| Formulation | |
|---|---|
| Components | Proportion |
| Thickening silica | 5.0 |
| Abrasive precipitated silica | Given in Table 1 |
| Sorbitol solution (70%) | 35.0 |
| Sulfosuccinate surfactant | Given in Table 1 |
| Saccharin sodium | 0.2 |
| Stevioside | 0.1 |
| Triclosan | 0.1 |
| Carboxymethyl cellulose sodium | 1.0 |
| Flavor | 0.9 |
| Water | Balance |
| Total | 100.0 |

Evaluation Method (Stain Formation Inhibitory Effect)

A hydroxyapatite disk with a diameter of 1 cm was used as a dental model, and was immersed successively in human saliva (10 minutes), 0.2% aqueous chlorhexidine gluconate solution (2 minutes), a supernatant of 4-fold diluted slurry of the toothpastes to be tested (2 minutes), 0.3% aqueous ammonium iron (III) citrate solution (2 minutes), and tea extract (10 minutes), and the immersion cycle was repeated 10 times. Then, the color difference of the respective disk before and after the experiment was measured (the color difference being referred to as dE). Color difference when using distilled water instead of toothpaste (referred to as dE0) was measured as control value, and the degree of stain formation inhibition was calculated by the following formula:

Degree of stain formation inhibition (%)=(dE0−dE)× 100/dE0.

Color difference meter CR-241 (made by Minolta) was used for measurement of color differences.

When the degree of stain formation inhibition is large, high effects can be attained. The degree of inhibiting stain formation is categorized as follows: the range from 0% inclusive to 50% exclusive is defined as "c", the range from 50% inclusive to 70% exclusive is defined as "b", and the range from 70% inclusive to 100% inclusive is defined as "a".

(Stain Deposition Suppressive Effect)

A 4 mm square buccal enamel test-piece was obtained from a bovine mandibular central incisor teeth and was embedded in transparent polyester resin. Subsequently, the surface of the enamel test-piece was smoothed with sandpaper and was subjected to mirror-plane polishing using alumina. The surface of the enamel test-piece was immersed in 0.2 mol/l hydrochloric acid for 60 seconds, and was then immersed in aqueous saturated sodium carbonate solution for 30 seconds, and subsequently was immersed in 1% aqueous phytic acid solution for 60 seconds. It was washed with ion-exchanged water and was used as a specimen. The specimen was set to a brushing machine conforming to BSI which had a commercial toothbrush (nylon hair) installed. The brushing machine was caused to move back and forth 1000 times under pressure of 150 g in the 4-fold diluted slurry of toothpastes to be tested, and the specimen was washed with ion-exchanged water. Separately, about 5 g of tea leaves was put into 1000 ml of ion-exchanged water and the mixture was infused for 10 minutes to obtain a solution. Then, a stain culture medium was prepared in the obtained solution by dissolving about 3.4 g of instant tea, about 2.5 g of pig stomach mucin, and about 1.0 g of iron (III) chloride hexahydtrate were dissolved. The specimen was immersed in the prepared stain culture medium at room temperature and then air-dried, which was repeated about every 30 seconds for 1 hour. Subsequently, the specimen was washed with ion-exchanged water, and was then air-dried for at least 1 hour. Thereafter, the discoloration degree of this specimen was evaluated visually based on the following criteria:

TABLE 1

| Components | Example I | | | | Comparative Example I | | | |
|---|---|---|---|---|---|---|---|---|
| | 1 | 2 | 3 | 4 | 1 | 2 | 3 | 4 |
| Disodium polyoxyethylene (2 mols) alkyl (12 to 14) sulfosuccinate | 1 | 1 | 0.5 | | 1 | | | |
| Disodium lauryl sulfosuccinate | | | | 0.5 | 0.5 | 0.5 | | |
| Abrasive precipitated silica A | 2 | 3 | 2 | 8 | | | 1 | |
| Abrasive precipitated silica B | 15 | 17 | 20 | | | 10 | 10 | |
| [Evaluation results] | | | | | | | | |
| Stain formation inhibition | a | a | a | b | b | a | c | C |
| Stain deposition inhibition | a | a | a | a | d | c | b | D | a: Substantially no discoloration
b: Slight discoloration
c: Moderate discoloration
d: Considerable discoloration As shown in Table 1, toothpastes containing sulfosuccinate surfactant and abrasive precipitated silica having $d_{50}$ of 5 μl or less, $d_{90}$ of 15 μm or less, and the RDA value of 120 or more (abrasive precipitated silica A) exhibited high stain formation inhibitory and stain deposition suppressive effects. Toothpastes further containing abrasive precipitated silica B are improved in stain formation inhibitory effect as compared to the toothpastes containing the abrasive precipitated silica A only.

Example I-5

Toothpastes were prepared by the following formula according to a known procedure.

| Components | Proportion (%) |
|---|---|
| Abrasive precipitated silica A | 2.0 |
| Abrasive precipitated silica B | 18.0 |
| Sorbitol solution (70%) | 30.0 |
| Glycerin | 10.0 |
| Titanium oxide | 0.5 |
| Polyethylene glycol 400 | 3.0 |
| Carboxymethyl cellulose sodium | 1.0 |
| Sodium lauryl sulfate | 1.0 |
| Polyoxyethylene (60) hydrogenated-castor oil | 1.0 |
| Disodium polyoxyethylene (2-mols) alkyl (12 to 14) sulfosuccinate | 1.0 |
| Sodium fluoride | 0.2 |
| Isopropyl methylphenol | 0.05 |
| Flavor | 1.0 |

-continued

| Components | Proportion (%) |
|---|---|
| Saccharin sodium | 0.2 |
| Stevia extract | 0.1 |
| Water | balance |
| Total | 100.0 |

Example I-6

Toothpastes were prepared by the following formula according to a known procedure.

| Components | Proportion (%) |
|---|---|
| Secondary calcium phosphate dihydrate | 15.0 |
| Abrasive precipitated silica C | 8.0 |
| Thickening silica | 5.0 |
| Carboxymethyl cellulose sodium | 1.0 |
| Sodium lauryl sulfate | 1.2 |
| Disodium lauryl sulfosuccinate | 2.0 |
| Flavor | 0.9 |
| Benzylsuccinate | 0.01 |
| Saccharin sodium | 0.2 |
| Stevia extract | 0.04 |
| Water | balance |
| Total | 100.0 |

The toothpastes prepared in Examples I-5 and I-6 had excellent stain formation inhibitory and stain deposition suppressive effects.

The present invention can provide an oral composition which has both stain formation inhibitory and stain deposition suppressive effects, and thus effectively prevents tooth discoloration.

Examples II-1 to II-4

Toothpastes were prepared by mixing the components shown below according to a known procedure, and was used to evaluate bitterness and surfactant odor.

| | Formulation | |
|---|---|---|
| Components | Proportion (%) | |
| Abrasive precipitated silica A | 3.0 |
| Abrasive precipitated silica B | 15.0 |
| Thickening silica | 5.0 |
| Sorbitol solution (70%) | 35.0 |
| Sulfosuccinate surfactant | Given in able 2 |
| Saccharin sodium | Given in Table 2 |
| Stevioside | Given in Table 2 |
| Triclosan | 0.1 |
| Carboxymethyl cellulose sodium | 1.0 |
| Vanillin | Given in Table 2 |
| Anethole | Given in Table 2 |

-continued

| Formulation | |
|---|---|
| Components | Proportion (%) |
| Benzylsuccinate | Given in Table 2 |
| Flavor | 0.9 |
| Water | Balance |
| Total | 100.0 |

Evaluation Method (Evaluation of Bitterness)

Bitterness was evaluated on a scale of 1 to 5, when brushing teeth by the toothpastes tested:
1: No bitterness
2: Substantially no bitterness
3: Slight bitterness
4: Mild bitterness
5: Considerable bitterness.

Strength of bitterness was categorized by the total of the scores given by 5 panelists as follows: 5 to 10 as "a", 11 to 15 as "b", 16 or more as "c". A high score shows that bitterness is strong.

(Evaluation of Surfactant Odor)

Evaluation of surfactant odor was evaluated on a scale of 1 to 5 when washing teeth with toothpastes tested:
1: No surfactant odor
2: Substantially no surfactant odor
3: Slight surfactant odor
4: Moderate surfactant odor
5: Considerable surfactant odor Strength of surfactant odor was categorized by the total of the scores given by 5 panelists as follows: 5 to 10 as "a", 11 to 15 as "b", 16 or more as "c". A high score shows that surfactant odor is strong.

These evaluation results are shown in Table 2.

TABLE 2

| | Example II | | | |
|---|---|---|---|---|
| Components | 1 | 2 | 3 | 4 |
| Disodium polyoxyethylene (2 mols) alkyl (12~14) sulfosuccinate | 1 | 1 | 0.5 | |
| Disodium lauryl sulfosuccinate | | | 0.5 | 0.5 |
| Saccharin sodium | 0.15 | 0.2 | 0.15 | 0.3 |
| Stevioside | 0.15 | 0.08 | 0.05 | 0.04 |
| Anethole | 0.01 | 0.01 | | 0.01 |
| Vanillin | | 0.01 | | 0.01 |
| Benzylsuccinate | | | 0.01 | 0.01 |
| [Evaluation results] | | | | |
| Bitterness | a | a | a | a |
| Surfactant odor | a | a | a | a |

As shown in Table 2, toothpastes were prepared by containing 0.01% inclusive to 1% exclusive of saccharin sodium and stevia extract in a weight ratio of saccharin sodium: stevia extract from 1:1 to 8:1, and further containing one or more flavor compounds selected from vanillin, anethole, and benzylsuccinate. Such toothpastes had little bitterness and little surfactant odor. All toothpastes shown in Table 2 were endowed with stain formation inhibitory and stain deposition suppressive effects.

Example II-5

Toothpastes were prepared by the following formula according to a known procedure.

| Components | Proportion (%) |
|---|---|
| Calcium carbonate | 30.0 |
| Abrasive precipitated silica A | 3.0 |
| Sorbitol solution (70%) | 30.0 |
| Carboxymethyl cellulose sodium | 1.0 |
| Sodium lauryl sulfate | 1.2 |
| Disodium lauryl sulfosuccinate | 2.0 |
| N-lauroyl sarcosine sodium | 0.1 |
| Flavor | 0.9 |
| Vanilla oil (containing vanillin) | 0.01 |
| Anethole | 0.05 |
| Benzylsuccinate | 0.01 |
| Saccharin sodium | 0.2 |
| Stevia extract (stevioside content 70%) | 0.04 |
| Water | balance |
| Total | 100.0 |

Example II-6

Toothpastes were prepared by the following formula according to a known procedure.

| Components | Proportion (%) |
|---|---|
| Abrasive precipitated silica B | 10.0 |
| Abrasive precipitated silica C | 4.0 |
| Thickening silica | 6.0 |
| Sorbitol solution (70%) | 30.0 |
| Glycerin | 10.0 |
| Titanium oxide | 0.5 |
| Polyethylene glycol 400 | 3.0 |
| Carboxymethyl cellulose sodium | 1.0 |
| Sodium lauryl sulfate | 1.0 |
| Polyoxyethylene (60) hydrogenated castor oil | 1.0 |
| Disodium polyoxyethylene (2 mols) alkyl (12~14) sulfosuccinate | 1.0 |
| Sodium fluoride | 0.2 |
| Isopropyl methyl phenol | 0.05 |
| Flavor | 0.9 |
| Vanillin | 0.02 |
| Star anise oil (containing anethole) | 0.03 |
| Saccharin sodium | 0.2 |
| Stevia extract (stevioside content 50%) | 0.1 |
| Water | balance |
| Total | 100.0 |

The oral compositions prepared in Examples II-5 and II-6 exhibited the effects of inhibiting stain formation and stain deposition, and also reducing bitterness and surfactant odor.

The present invention can provide an oral composition which effectively inhibits stain formation and stain deposition, and thus teeth can be maintained aesthetically favorable, and moreover can provide an oral composition which is free from both bitterness and surfactant odor, and thus is pleasant to use.

The invention claimed is:

1. An oral composition comprising 0.5 to 10% by weight of said oral composition of an abrasive precipitated silica having a 50 percentile ($d_{50}$) of particle diameter being 5 μm or less, a 90 percentile ($d_{90}$) of particle diameter being 15 μm or less and an RDA value of 120 or more, and 0.01 to 5% by weight of said oral composition of at least one of sulfosuccinate surfactants represented by general formula (1):

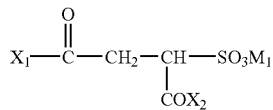

wherein either $X_1$ or $X_2$ is $R_1\text{---}(AO)_n\text{---}$ or $R_1CO\text{---}B\text{---}(AO)_n\text{---}$ and the other is $M_2O\text{---}$; $M_1$ and $M_2$ are the same or different and each represent hydrogen, alkali metal, alkaline earth metal, ammonium, or alkanolamine; $R_1$ is alkyl or alkenyl with 8 to 22 carbons; AO is oxyalkylene with 2 or 3 carbons and the average number of moles of AO addition polymerization, "n", is 0 to 20; and B is ---NH--- or a monoalkanolamine residue with 2 or 3 carbons.

2. An oral composition according to claim 1, wherein the average number of moles of AO addition polymerization, "n", of sulfosuccinate surfactant represented by general formula (1) is 0 to 7.

3. An oral composition according to claim 1 wherein a carbon number of an alkyl group or an alkenyl group of sulfosuccinate surfactant represented by general formula (1) is 10 to 14.

4. An oral composition according to claim 1 wherein $M_1$ and $M_2$ of sulfosuccinate surfactant represented by general formula (1) are sodium.

5. An oral composition according to claim 1 wherein an RDA value of the abrasive precipitated silica is 130 to 200.

6. An oral composition according to claim 1 wherein the amount of the abrasive precipitated silica is 1 to 5% by weight of said oral composition.

7. An oral composition according to claim 1 further comprising an abrasive precipitated silica having an RDA value of 40 to 110.

8. An oral composition according to claim 7 wherein the amount of the abrasive precipitated silica having an RDA value of 40 to 110 is 3 to 25% by weight of said oral composition.

9. An oral composition according to claim 1 wherein saccharin sodium and stevioside are further contained in the weight ratio of saccharin sodium to stevioside of 1:1 to 8:1 and their total amount is 0.01 to 1% by weight of oral composition.

10. An oral composition according to claim 1 further comprising at least one member selected from the group consisting of vanillin, anethole, and benzylsuccinate.

11. An oral composition according to claim 9 further comprising at least one member selected from the group consisting of vanillin, anethole, and benzylsuccinate.

12. An oral composition according to claim 7, wherein the 50 percentile ($d_{50}$) particle diameter of the silica having an RDA value of 40 to 110 is 20 μm or less.

13. An oral composition according to claim 7, wherein the 50 percentile ($d_{50}$) particle diameter of the silica having an RDA value of 40 to 110 is 8 to 20 μm.

14. An oral composition according to claim 7, wherein the 50 percentile ($d_{50}$) particle diameter of the silica having an RDA value of 40 to 110 is 10 to 20 μm.

15. An oral composition according to claim 8, wherein the 50 percentile ($d_{50}$) particle diameter of the silica having an RDA value of 40 to 110 is 20 μm or less.

16. An oral composition according to claim 8, wherein the 50 percentile ($d_{50}$) particle diameter of the silica having an RDA value of 40 to 110 is 8 to 20 μm.

17. An oral composition according to claim 8, wherein the 50 percentile ($d_{50}$) particle diameter of the silica having an RDA value of 40 to 110 is 10 to 20 μm.

* * * * *

UNITED STATES PATENT AND TRADEMARK OFFICE
CERTIFICATE OF CORRECTION

PATENT NO.        : 7,166,272 B2
APPLICATION NO. : 10/481853
DATED             : January 23, 2007
INVENTOR(S)       : Koichi Fujisawa It is certified that error appears in the above-identified patent and that said Letters Patent is hereby corrected as shown below:

On Title Page, at Column 2, Line 2, Item (57); in Abstract section, please delete "(d50)" and insert -- $(d_{50})$ --, therefor.

On Title Page, at Column 2, Line 3, Item (57); in Abstract section, please delete "(d90)" and insert -- $(d_{90})$ --, therefor.

At Column 4, Line 48 (approximately), please delete "hefferen" and insert -- Hefferen --, therefor.

At Column 6, Line 3, please delete "phophate" and insert -- phosphate --, therefor.

At Column 7, Line 26, after "below)" please insert -- . --.

At Column 9, Line 14 (approximately), after "(3)" please insert -- : --.

At Column 9, Line 50, please delete "µl," and insert -- µm, --, therefor.

At Column 11, Line 37, please delete "µl" and insert -- µm --, therefor.

At Column 15, Line 12, please delete "$R_1$" and insert -- $R_1O$ --, therefor.

At Column 16, Line 9 (approximately), after "of" please insert -- said --.

Signed and Sealed this

Twelfth Day of August, 2008

JON W. DUDAS
*Director of the United States Patent and Trademark Office*